(12) United States Patent
Baehre et al.

(10) Patent No.: US 8,777,618 B2
(45) Date of Patent: Jul. 15, 2014

(54) MEDICAL IMPLANT II

(75) Inventors: Wolf-Friedrich Baehre, Isernhagen (DE); Kurt Ruffieux, Thalwil (CH)

(73) Assignee: Synergy Biosurgical AG, Zug (CH)

( * ) Notice: Subject to any disclaimer, the term of this patent is extended or adjusted under 35 U.S.C. 154(b) by 369 days.

(21) Appl. No.: 12/677,006

(22) PCT Filed: Sep. 17, 2007

(86) PCT No.: PCT/CH2007/000454
§ 371 (c)(1),
(2), (4) Date: Jun. 9, 2010

(87) PCT Pub. No.: WO2009/036576
PCT Pub. Date: Mar. 26, 2009

(65) Prior Publication Data
US 2012/0129131 A1 May 24, 2012

(51) Int. Cl.
*A61C 8/00* (2006.01)
(52) U.S. Cl.
USPC ........................................ 433/201.1
(58) Field of Classification Search
CPC ............... A61F 2250/0091; A61F 2310/00796
USPC ........... 433/201.1, 172–176, 202.1, 215, 220, 433/221; 606/5; 623/23.76, 6.59, 23.5, 623/17.16, 23.51, 20.16; 604/8; 600/37
See application file for complete search history.

(56) References Cited

U.S. PATENT DOCUMENTS

| | | | |
|---|---|---|---|
| 4,506,681 A | 3/1985 | Mundell | |
| 4,525,147 A | 6/1985 | Pitz et al. | |
| 5,037,442 A | 8/1991 | Wintermantel et al. | |
| 5,163,960 A * | 11/1992 | Bonutti | 128/898 |
| 5,290,281 A | 3/1994 | Tschakaloff | |
| 5,662,712 A | 9/1997 | Pathak et al. | |
| 5,843,186 A | 12/1998 | Christ | |
| 5,879,387 A | 3/1999 | Jones et al. | |
| 6,080,161 A | 6/2000 | Eaves, III et al. | |
| 6,749,556 B2 | 6/2004 | Banik | |
| 6,875,427 B1 * | 4/2005 | DeVore et al. | 424/78.03 |
| 7,182,783 B2 | 2/2007 | Trieu | |

(Continued)

FOREIGN PATENT DOCUMENTS

| | | |
|---|---|---|
| CO | 6270194 | 4/2011 |
| EP | 0268179 | 5/1988 |

(Continued)

OTHER PUBLICATIONS

"International Application Serial No. PCT/CH2007/000454, International Search Report mailed Jun. 17, 2008", (w/ English Translation), 8 pgs.

(Continued)

*Primary Examiner* — Cris L Rodriguez
*Assistant Examiner* — Mirayda A Aponte
(74) *Attorney, Agent, or Firm* — Baker & Hostetler LLP

(57) ABSTRACT

A medical implant for insertion into bone including a zone sensitive to electromagnetic radiation from a radiation source, the zone comprising a polymer material configured to transition from a solid condition to a softened condition when the zone is exposed to the electromagnetic radiation and being flowable into interspaces of the bone in the softened condition, and a light-conducting portion configured to conduct the electromagnetic radiation from the radiation source to the zone when the medical implant is inserted into the bone.

32 Claims, 7 Drawing Sheets

(56) References Cited

U.S. PATENT DOCUMENTS

Figure 1:
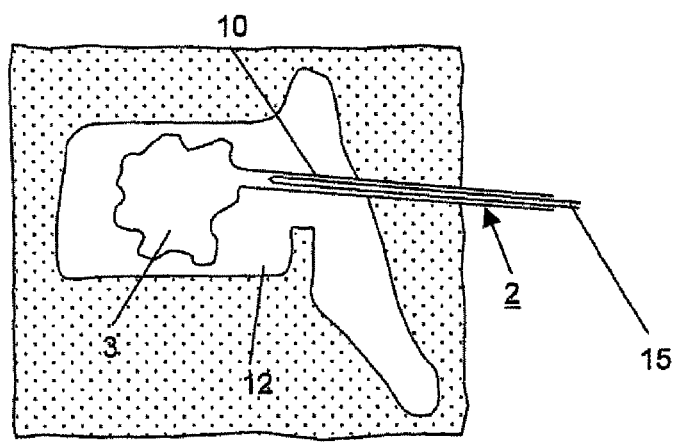

| | | |
|---|---|---|
| 7,294,187 B2 | 11/2007 | Chow et al. |
| 7,740,656 B2 | 6/2010 | Mensah et al. |
| 7,780,705 B2 | 8/2010 | Shaolian et al. |
| 7,824,444 B2 | 11/2010 | Biscup et al. |
| 7,993,404 B2 | 8/2011 | Trieu |
| 2004/0030341 A1 | 2/2004 | Aeschlimann et al. |
| 2004/0230309 A1 | 11/2004 | DiMauro et al. |
| 2005/0008620 A1* | 1/2005 | Shimp et al. .................. 424/93.7 |
| 2005/0102017 A1 | 5/2005 | Mattison |
| 2005/0107872 A1 | 5/2005 | Mensah et al. |
| 2005/0234289 A1 | 10/2005 | Anstadt et al. |
| 2006/0064170 A1 | 3/2006 | Smith et al. |
| 2006/0095138 A1* | 5/2006 | Truckai et al. ............. 623/23.62 |
| 2006/0229628 A1 | 10/2006 | Truckai et al. |
| 2006/0241768 A1 | 10/2006 | Trieu |
| 2007/0233250 A1 | 10/2007 | Shadduck |
| 2007/0270953 A1 | 11/2007 | Trieu |
| 2008/0195227 A1 | 8/2008 | Boling et al. |
| 2008/0269745 A1 | 10/2008 | Justin |
| 2010/0241229 A1 | 9/2010 | Baehre et al. |
| 2011/0160870 A1 | 6/2011 | Baumgartner et al. |
| 2012/0041557 A1 | 2/2012 | Frigg |

FOREIGN PATENT DOCUMENTS

| | | |
|---|---|---|
| EP | 0358601 | 3/1990 |
| EP | 0696185 B1 | 2/1996 |
| EP | 698382 A2 * | 2/1996 |
| EP | 0698382 A2 | 2/1996 |
| EP | 1000958 | 5/2000 |
| EP | 1421921 | 5/2004 |
| EP | 1454602 A1 * | 9/2004 |
| EP | 1454602 A1 | 9/2004 |
| JP | 02/167159 | 6/1990 |
| JP | 08/506027 | 7/1996 |
| JP | 08-509642 | 10/1996 |
| JP | 9/511666 | 11/1997 |
| JP | 2004-513697 | 5/2004 |
| JP | 2006-502805 | 1/2006 |
| WO | WO 94/11058 | 5/1994 |
| WO | 95/28124 | 10/1995 |
| WO | WO 01/47337 | 7/2001 |
| WO | 02/39875 | 5/2002 |
| WO | WO 02/069817 | 9/2002 |
| WO | WO 2004/016205 | 2/2004 |
| WO | 2004/034917 | 4/2004 |
| WO | WO-2006002569 A1 | 1/2006 |
| WO | WO 2006/069677 | 7/2006 |
| WO | WO-2007092869 A2 | 8/2007 |
| WO | WO 2008/079864 | 7/2008 |
| WO | WO 2008/112912 | 9/2008 |
| WO | 2009/003294 | 1/2009 |
| WO | WO 2009/013752 | 1/2009 |
| WO | WO 2009/036576 | 3/2009 |
| WO | WO 2011/066522 | 6/2011 |
| WO | WO 2012/021148 | 2/2012 |

OTHER PUBLICATIONS

EPO Communication dated Mar. 8, 2012 for European Patent Application No. 07 800 645.9.

Response filed with the European Patent Office for European Patent Application No. 07 800 645.9, dated Jun. 20, 2012.

Japanese Patent Application No. 2010-513597: Office Action dated Nov. 8, 2013, 4 pages (English Translation Only).

* cited by examiner

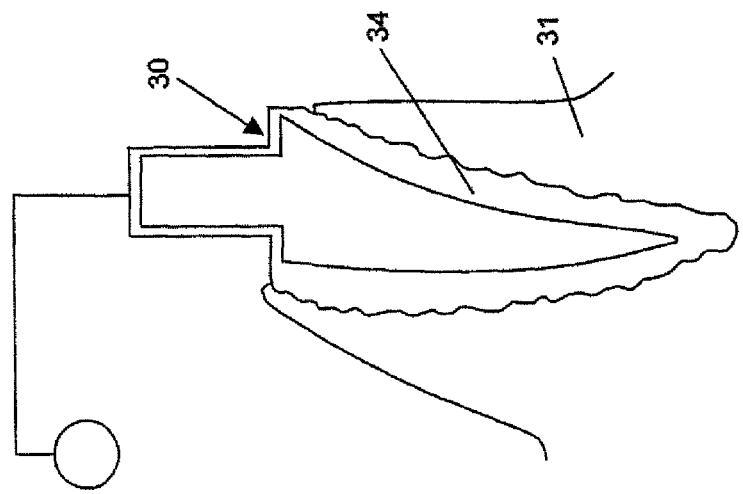
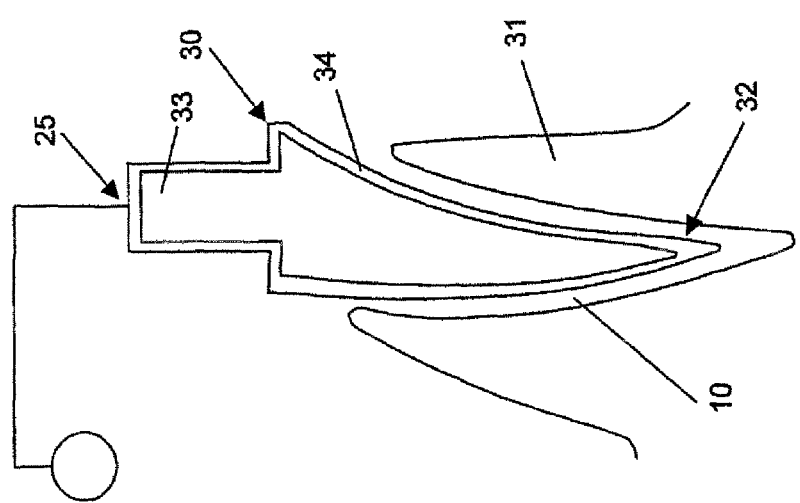

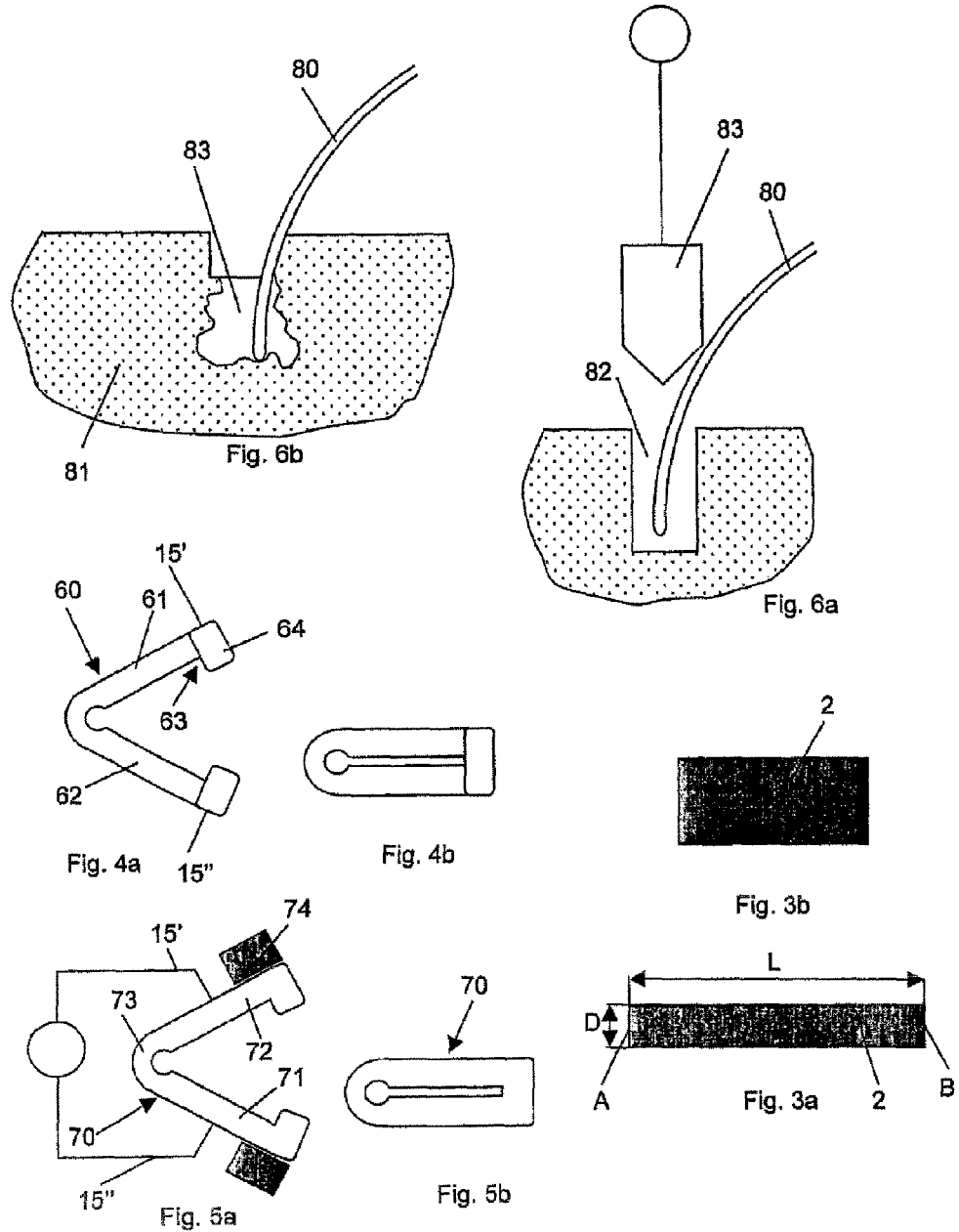

MEDICAL IMPLANT II

RELATED APPLICATION

This patent application is a U.S. National Stage Filing under 35 U.S.C. 371 from International Patent Application Serial No. PCT/CH2007/000454, filed Sep. 17, 2007, and published on Mar. 26, 2009, as WO 2009/036576 A1, the contents of which are incorporated herein by reference in their entirety.

The invention refers to a medical implant, a device for the fixation of bones or bone fragments, a process for producing the inventive medical implant, a process for coating the inventive medical implant, an osteosynthesis process, and the use of the inventive medical implant.

STATE OF THE ART

The use of biocompatible, thermoplastic materials for osteosynthetic and similar processes for fastening purposes on human or animal bones is a known state of the art and has been attempted in various ways, for instance by an external application of heat such as by a hot gluing pistol (for instance U.S. Pat. No. 5,290,281) or by liquefying a polymer by ultrasound wave energy according to WO2006/002569 Woodwelding. These techniques are however affected by disadvantages: the warming-up by external heat sources—such as by a hot gluing pistol—means that an implant must be inserted very quickly so as not to cool off while undergoing a connection with the bones, because it typically has only a small thermal capacity, and the fact that a thermoplastic material can penetrate into bone interspaces only in a softened condition. As soon as the material has cooled off, no further connection with the bone occurs. Even the necessary excessive warming-up of the thermoplastic material—in order to prevent a premature solidification—is disadvantageous, because it causes damage to both the material and the (bone) tissue.

The EP-B 0 696 185 by Pathak has made known a polymeric, chromophore-containing medical implant capable of being impacted with laser light so that, thanks to the absorbed electromagnetic radiation, the entire implant including its surface can be softened. The medical implant mentioned there (as a vascular stent) is inserted into the human body by using a catheter. The disadvantage of this system is that the entire implant is softened, so that because of this structural weakening an inserting of the implant by force becomes impossible. The described implant is moreover, because of its mentioned shape and the fact that in the described design it is softened in its entirety, unsuitable for achieving an osteosynthesis as in the present invention. The Pathak invention in particular requires an external application of force (by a balloon catheter) in order to deform the implant (a vascular stent).

The U.S. Pat. No. 5,163,960 by Bonutti et al. has made known a process for producing an implant by warming-up one or more plastic components by using a laser (or other warming-up sources) for the purpose of their mutual gluing or connecting with a metallic implant. This already known process is not applicable in surgery, where the task consists of squeezing a partially softened bone implant in a borehole in the bone, so that the softened plastic can penetrate into the irregularities of the bone wall and induce a geometric coupling with the same.

This is where the invention will provide a remedy. The task underlying the invention is to create a medical implant capable, when irradiated with electromagnetic radiation energy, of being only partially warmed-up and softened at defined points, so that the implant can be inserted under pressure in a cavity, such as for instance a bone cavity, adapt to the geometry of the cavity and be inserted under pressure in the interspaces surrounding the implant in the bone, so that after the polymer's cooling and solidifying, the implant may remain anchored by geometric coupling.

The medical implant according to the invention can be realized in various implant forms, in particular as a screw, pin, clip, prong, plate, nail, spiking wire, cage, pedicle screw (or nail), piercing, skin attachment, medicine carrier, gene material carrier, bioactive factor carrier (for instance growth factors, bone formation promoting substances, pain killers, etc.), as carriers of other implants, as a dowel, clamp, pearl, dental implant, dental root implant, hose, tube, thread, thread in a hose or tube, tissue, web, skeleton, stocking, band, loose fibers, fibrous knot, fibrous flocks, granulate, chain, and anchor with or without a threading eyelet.

The invention solves the intended task by using the inventive medical implant, by using a device for fixating bones or bone fragments, a process for producing the medical implant, a process for coating the medical implant, an osteosynthesis process, and the usage of the inventive medical implant.

An essential advantage of the invention lies in the tact that it can be further warmed-up even while being inserted into the bone, and still retain its internal mechanical stability.

The medical implant according to the invention utilizes the effect that thanks to electromagnetic radiation energy, an energy is transferred to the excitable electrons in the chromophore, in the polymer itself or in the color coating, which later induces a warming-up and eventually a softening of the polymer in this region, while non-excitable regions in the implant are not warmed-up or softened.

The following definitions apply to the following terms frequently employed in the entire description:

Fusing/softening/plasticizing: Fusing, softening or plasticizing of the implant material according to the invention is intended to mean that the softening of the implant occurs by the heat generated by the absorption of radiation, to the point that allows the previously not usefully (typically by hand) plastically deformable implant in the body to be deformed and employed in a way according to the invention.

Photoconductor: The term photoconductor is on one hand intended to mean flexible or rigid optical light-conducting structures, such as for instance glass fiber cables, reflecting hoses (e.g. also nano-tubes) conducting light and used to transmit electromagnetic radiation from the source to the implant. On the other hand, the implant itself may serve as a photoconductor and light diffuser. After entering the implant, the light is conducted through the implant until it arrives at the point where the softening of the polymer, mostly at its surface, is to take place. In order to conduct the light through the photoconductor in the implant up to the desired point, the photoconductor in the implant may on one hand actually conduct the light, meaning for instance to the tip of a pin and then distribute it there, so as to reach the surface of the pin, for instance by diffusion.

Photoconductivity/light transmittance: This is generally based on optically transparent implants capable of transmitting electromagnetic radiation, for instance like glass. This photoconductivity may also be specific for the radiation introduced, or other wavelengths may be reflected or absorbed. It may however be desirable, in certain embodiments of the invention, that certain areas in or on the implant should be able to diffuse light, so as to achieve a uniform distribution of the light. This diffusing effect may be achieved by using crystals, bubbles, fractures, phase boundaries of any kind, foreign bodies or pigments of any kind, or admixtures of polymers of all sorts. In particular, ceramic substances, such as particulates of calcium phosphate are also worth mentioning.

Light source: All sources of electromagnetic radiation can be considered as suitable light sources, such as incandescent light bulbs, vapor emission lamps, diodes, semiconductors, sparks, flames, sunlight etc. Diodes and laser light sources, for instance the following, are particularly preferred:

Laser types: Lasers are preferred sources of energy, as they are typically emitting only a few narrowly defined frequencies of electromagnetic radiation. The absorption spectra of one chromophore (or several, up to many chromophores) of the non absorbing portion of the implant as well as of the body's surroundings may thus be tuned-up to each other. In a preferred application, the laser radiates in a preferably monochromatic frequency that is barely absorbed by the implant, strongly by the chromophore, and again only barely by the surroundings. This makes it possible to supply different areas with different chromophores in the implant, and to specifically warm them up with the electromagnetic radiation frequency that may be preferred on a case-by-case basis.

One or more of the radiation frequencies that are especially well absorbed by the chromophore pigment in the polymer or by the light absorbing polymer are particularly preferred.

All currently used laser types, swinging modes, pulsating or continuous wave operations should be included and are in themselves possible. The preferred types are diode lasers of the infrared or visible spectrum. Under certain conditions it is also desirable to employ polarized radiation, for instance by employing polarization filters in the implant or on the radiating source, or for instance electromagnetic radiation already generated in a polarized form. The polarization can thus be utilized as a means for selecting the targeted warming-up of the implant, especially when employing chromophores that are preferably excitable by polarized light.

The preferred wavelength of electromagnetic radiation lies in the range between 260 and 3,000 nm, preferably in the visible range and in the near infrared range of up to 1,200 nm. However, other wavelengths are also conceivable. The shape of the light radiation may be of any kind, such as with a cross section of an oval, rectangular, star-shaped, triangular, bundled-ray form, etc.

A non-exhaustive list of employable lasers is herewith given:

|  | Wavelength(s) |
|---|---|
| Gas laser | |
| Helium-neon laser | 632.8 nm (543.5 nm, 593.9 nm, 611.8 nm, 1.1523 μm, 1.52 μm, 3.3913 μm |
| Argon laser | 454.6 nm, 488.0 nm, 514.5 nm (351 nm, 457.9 nm, 465.8 nm, 476.5 nm, 472.7 nm, 528.7 nm) |
| Krypton laser | 416 nm, 530.9 nm, 568.2 nm, 647.1 nm, 676.4 nm, 752.5 nm, 799.3 nm |
| Xenon ion laser | Various wavelengths from UV to infrared |
| Nitrogen laser | 337.1 nm |
| Carbon dioxide laser | 10.6 μm (9.4 μm) |
| Carbon monoxide laser | 2.6 to 4 μm, 4.8 to 8.3 μm |
| Exciter laser | 193 nm (ArF), 248 nm (KrF), 308 nm (XeCl), 353 nm (XeF) |
| Chemical lasers | |
| Hydrogen fluoride laser | 2.7 to 2.9 μm, |
| Deuterium fluoride laser | ≈3800 nm (3.6 to 4.2 μm) |
| COIL (Chemical oxygen-iodine laser) | 1.315 μm |
| Color laser | |
| Color laser | 390-435 nm (stilbene), 460-515 nm (coumarin 102), 570-640 nm (rhodamine 6G), and others |
| Metal-vapor laser | |
| Helium-cadmium (HeCd) metal-vapor laser | 441.563 nm, 325 nm |
| Helium-mercury (HeHg) metal-vapor laser | 567 nm, 615 nm |
| Helium-selenium (HeSe) metal-vapor laser | up to 24 wavelengths between red and UV |
| Copper-vapor laser | 510.6 nm, 578.2 nm |
| Gold-vapor laser | 627 nm |
| Solid material laser | |
| Ruby laser | 694.3 nm |
| Nd:YAG laser | 1.064 μm, (1.32 μm) |
| Er:YAG laser | 2.94 μm |
| Neodymium YLF (Nd:YLF) solid material laser | 11.047 and 1.053 μm |
| Neodymium-doped yttrium orthovanadate (Nd:YVO$_4$) laser | 1.064 μm |
| Neodymium-doped yttrium calcium oxoborate laser, Nd:YCa$_4$O(BO$_3$)$_3$ or simply Nd:YCOB | ≈1.060 μm (≈530 nm at the second harmonic) |
| Neodymium glass (Nd:glass) laser | ≈1.062 μm (silicate glasses), ≈1.054 μm (phosphate glasses) |
| Titanium sapphire (Ti:sapphire) laser | 650-1100 nm |
| Thulium YAG (Tm:YAG) laser | 2.0 μm |
| Ytterbium YAG (Yb:YAG) laser | 1.03 μm |
| Ytterbium doped glass laser (rod, plate/chip, and fiber) | 1 μm |
| Holmium YAG (Ho:YAG) laser | 2.1 μm |
| Cerium-doped lithium strontium (or calcium) aluminum fluoride (Ce:LiSAF, Ce:LiCAF) | ≈280 to 316 nm |
| Promethium 147 doped phosphate glass ($^{147}$Pm$^{+3}$:Glass) solid-state laser | 933 nm, 1098 nm |

| | Wavelength(s) |
|---|---|
| Chromium doped chrysoberyl (alexandrite) laser | Typically 700 to 820 nm |
| Erbium doped and erbium-ytterbium codoped glass lasers | 1.53-1.56 μm |
| Trivalent uranium doped calcium fluoride (U:CaF$_2$) solid state laser | 2.5 μm |
| Divalent samarium doped calcium fluoride (Sm:CaF$_2$) laser | 708.5 nm |
| F-center laser | 2.3-3.3 μm |
| Semiconductor laser | |
| Semiconductor laser diode | 0.4-20 μm, depending on the material |
| GaN | 0.4 μm |
| AlGaAs | 0.63-0.9 μm |
| InGaAsP | 1.0-2.1 μm |
| Lead salt | 3-20 μm |
| Vertical cavity surface emitting laser (VCSEL) | 850-1500 nm, depending on the material |
| Quantum cascade laser | Infrared |
| DPSS-lase | UV-infrared |
| Hybrid silicon laser | Infrared |

Absorption of electromagnetic radiation: The term absorption of electromagnetic radiation is to mean that at the point where the absorption occurs, the implant typically (but not necessarily) absorbs at least twice as much irradiated energy as in the areas without absorption. Typically, however, a factor of 5-1000 times more energy is absorbed in the energy-absorbing area with respect to the area where the implant is non-absorbing.

As an absolute value, in the non-absorbing area the implant absorbs 0-10% of the irradiated energy, the area with the chromophore 50-100% of the energy, and the residual energy leaves the implant in the surroundings.

Chromophore: The term chromophore stands to mean coloring substances or pigments added to the polymer to absorb the electromagnetic radiation and convert it to heat.

A special application also allows employing substances that are added to the implant or coating it, without having chromophore properties. However, while being introduced into the body these substances change upon contact with the same, preferably as a reaction to the pH of the tissue, to body salts, body moisture or body temperature, and this discolors the substance and renders it absorbent for the electromagnetic radiation. The only area thus warming-up is that coming in contact with the body, because the implant discolors only at that point.

In general, the following chromophores and pigments should be explicitly included: chlorophyll, carbon black, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, and D&C yellow No. 10. A special case are the fluorescent chromophores that under certain circumstances do not absorb but radiate off light that is absorbed from the surroundings, the polymer or any additionally introduced chromophore.

Light-absorbing, non-colored polymer: Light-absorbing polymer stands to mean polymers having a property of their own to absorb light of a certain wavelength, without the need of adding a chromophore. In a special form of application, the polymer is warmed-up in advance to the point of discoloring spontaneously and thus becoming capable of absorbing more light. In an extreme case the polymer is partially carbonized or caramelized and thus becoming light-absorbent.

The absorption coefficient of the polymers is, like that of the chromophore, variable and must be set based on the indications. Indocyanine, for instance, has an absorption coefficient of 20,000 mg$^{-1}$ cm$^{-1}$. The resulting absorption coefficient of the chromophore obviously also depends on the concentration in the implant, a typical range is between 1,000 and 1,000,000 mol$^{-1}$ cm$^{-1}$.

Porous surface: The term porous surface stands to mean a surface which is suitable, after contacting the body's surface or body fluids such as for instance blood, for warming-up by irradiating it with an electromagnetic radiation. This occurs when upon contact with the body the implant is contaminated and becomes light-absorbing at the contaminated point. Before contacting the body, this particular embodiment of an implant has no or only a weak tendency to be warmed-up by electromagnetic radiation. Particularly suited for such a surface are rough, porous, uneven, spongy surfaces, which are eventually coated with hydrophilic, well absorbing materials such as for instance calcium phosphates, other ceramics, gypsum etc. It is alternatively also possible to apply structural elements through which body fluids are drawn or flow into the interior of the implant (for instance blood, through capillary forces) and absorbing light inside the same. As a result of the implant's deformation when pressed into the body or when creating the desired connection, the chromophore structures originating from the body are blended with the implant surface, thus reinforcing the local warming-up effect. As a peculiar effect, this also achieved the surprising effect that at a suitable wavelength even the implant's immediate neighborhood in the body was warmed-up, because the wavelength was chosen so that the body fluids contacting the implant, or the contacting body surface interacting with the implant's surface absorbed the electromagnetic radiation. It is however possible, through a suitable impulse duration and wavelength (or a combination of wavelengths) to achieve a warming-up only in the immediate neighborhood (<1 mm), without thus significantly damaging the tissue. This warming-up, which should preferably not exceed 100° C. and even more preferably 56° C., facilitates the softened thermoplastic material's flow into the interspaces of the body surface. This effect can also be achieved in the other embodiments mentioned above and below, when the employed electromagnetic radiation frequencies as well as the pulsating type, frequency and duration and the quantity of energy are appropriately chosen. According to the invention, the porous surface, for instance a calcium phosphate coating, is combined with a chromophore, either as an additional coating or as a mixture.

Reflectingly coated polymer: Reflecting coating stands to mean a polymer coating which inhibits the emission of electromagnetic radiation, so that the light is retained in the polymer and can warm-up the latter even at a low level of absorption (optionally even without a chromophore). However, the reflecting coating may also be used in combination with a chromophore and reinforce the action of the latter. In a further embodiment the implant can be reflected so as to prevent a premature emission of light from the implant, for instance to conduct the light toward the implant's tip. The reflection thus acts to reinforce the photo-conductance inside the implant.

The materials considered for a reflecting coating (which can also be worked into the interior of the polymer) include all light-reflecting substances, in particular metals and in turn especially metals compatible with the body, such as gold, titanium, platinum silver, steel and its alloys.

Frequency modulation: In order to achieve a local warming-up of the implant, there is also the possibility of introducing substances or optical elements into the implant which, while not significantly absorbing electromagnetic radiation, possess the property of shifting the frequency of light, such as typically frequency doubling crystals or frequency multiplying crystals. In this case, the long-wave light passes through the implant without materially warming it, up to the area with the frequency altering (normally doubling) characteristic without significantly warming it, then warms it and leaves the same, to a certain percentage, with a somewhat shorter frequency, while being absorbed to a significantly greater degree by the remainder of the implant. This effect can also be repeated several times. Typical substances for this effect are non-linear optical substances, for instance lithium niobate ($LiNbO_3$), potassium dihydrogen phosphate (KDP), beta-bariumborate ($\beta$-$BaB_2O_4$ or BBO), lithium triborate or DAST (diethylamino-sulfurtrifluoride). In a similar manner, even phase transitions or boundary layers having the same effect can be integrated in or on the implant.

Energy: The energy employed for a sufficient warm-up of the implant depends on its size, application and the locally given anatomical conditions. The typical average power of a light source is as follows: for small pins or fixation elements (of a diameter of 0.1-5 mm): about 0.1-50 Watt and preferably 0.5-10 Watt, and for the fixation of large prostheses or filling large bone defects 1-2,000 Watt.

The peak power during individually applied pulses may attain 5 kW and more. The target consists in softening a polymer having a softening volume V with an alternating current having a power density $P=0.005-5$ Watt/$mm^2$, within about 0.1-10 seconds.

The energy E thus applied equals about $E=0.0005-50$ Watt*seconds/$mm^3$.

The photoconductor can also be inserted into a borehole that penetrates the implant all the way to the opposite colored layer. If it is for instance desired to fuse only the colored layer, the uncolored layer, on which the front end of the photoconductor passed through the implant's borehole comes to rest, may present a thickness of 0.1-0.5 mm.

The medical implant according to the invention allows solving various tasks, some of which will be described in further detail, as follows:

Task A: Selective or Global Warming and Softening or Liquefying of Medical Implants by Using Electromagnetic Radiation During their Implantation.

The core of the pin is conceived so as not to warm-up at all or only partially, and to remain hard. At the same time, this core can serve as an optical element and transmit the light onward into the implant. The pin can then be pushed into a previously drilled hole which may be undersized, and the warmed-up, soft polymer is then pressed into the interspaces of the bone. After turning off the light source, the polymer (thermoplastic material) cools off and quickly hardens (<1-2 minutes), and the mechanical connection is established.

Task B: Selective or Overall Warming of a Thermoplastic Material Containing Implant to Achieve a Deformation During its Implantation.

In this case, a pin is, on its way, for instance supplied with a zone containing a dye, a self-coloring or a color layer and again impacted with an electromagnetic radiation. The pin warms up in the zone containing a dye, a self-coloring or a color layer. The pin can at this point deform in any desired manner.

Task C: Achieving a Local Fixation of a Polymer Implant in the Body.

Through a suitable production process, for instance by injection molding, the pin is provided with a strain of its own. Thanks to the warming-up of the entire pin, the thermoplastic material is relaxed and the pin shortens and increases in diameter, thus leading to a fixation in or on the surrounding tissue.

Task D: Achieving a Local Connection Between Multiple Implants by Welding them to Each Other.

This consists in connecting two thermoplastic implant elements which can be separately introduced into the body. This must guarantee that the necessary electromagnetic radiation can penetrate through both (or multiple) implant elements to be connected. In a typical case this means a granulate. After inserting the two (or multiple) implant elements, light radiation is admitted, the implant elements soften at their point of contact and can be joined by applying pressure. This way, however, it is also possible to glue up a thread, so as to renounce a knot.

Task E: Clamping or Enclosing Soft Tissues or Bones.

It is for instance possible to form a strip out of an implant material (an open ring) and to make it deformable and connected to a closed ring by supplying light. A polymer strip can likewise be employed as a forming material.

Task F: Production of Implants that can be Changed after Inserting into the Body, by Cutting the Implant Material Apart.

The implant material used and described herein can also be employed for the purpose of producing implants that can be selectively cut apart or opened. In this manner, a thread may for instance be cut with the aid of an electromagnetic radiation, particularly of great intensity, or preferably with a small but "sharp" lighting source. Dented or fused pins can thus for instance be cut off at the bone surface or modeled onto the same, until they fit flat on the surface of the bone. Medicine carriers can thus be opened to release their active ingredients.

Task G: Conducting Light Inside the Implant:

Inside the implant the light should be conducted to the zone where the softening is to be achieved, meaning where the light sensitive zone is present. This makes it possible to achieve a selective softening action even in implants that have a relatively uniform color, because the implant will be warming-up first at the point where it is present at its highest concentration.

Task H: Thermal Regulation:

The electromagnetic radiation must not excessively warm-up the implant and uniformly convert it to a warmed-up condition in the desired area. The temperature should not be over 500° C., preferably not over 250° C., and ideally remain below 100° C. The temperature can be controlled through the chromophore, which changes or loses its color above a certain critical temperature and thus slows down or stops absorbing the irradiated energy altogether (a so-called "thermochrome thermophore"). A homogeneous temperature distribution can on the other hand also be achieved by a pulsating input of energy. In the intervals without a pulsation, the energy has time to distribute inside the implant by heat conductance. Another possibility lies in measuring the local temperature and to appropriately adjust the power. The measuring can be done by using a temperature sensor, an infrared measurement using a photoconductor's camera, or by a Rutherford backscattering procedure. It is in particular possible to employ the photoconductor and the implant itself to measure heat radiation, meaning in a direction opposite that of feeding in the electromagnetic radiation. Possible means for this purpose are suitable optical elements such as semi-transparent mirrors in steel or other methods known to a specialist. A local overheating can also be achieved through a local or general cooling by using air, liquid or insulating zones (for instance zones with air-filled bubbles or ceramic particles such as insulators or the like). For this purpose and depending on the conditions, appropriate cooling channels must be available in the implant.

In a preferred form of embodiment, the color layer or reflecting layer has a thickness of at least 0.01 µm, and preferably a maximum of 2.5 µm.

In a further form of embodiment, the color layer or the reflecting layer has a thickness of a maximum 2.0 mm, and preferably a maximum of 0.6 mm.

A typical layer thickness to be applied in order to achieve a homogeneous layer around an implant lies in the range of 3-10 µm. If only the colored layer is to be fused, the suitable layer thickness to be introduced into the bone is in the range of 0.1 to 0.5 mm.

In a further form of embodiment the implant consists at least partially of a polymer to be warmed-up, which exhibits a minimum molar heat capacity $c_p$ of 1.6 kJ/kmolK, and preferably of 2.2 kJ/kmolK.

In a further form of embodiment the implant consists at least partially of a polymer to be warmed-up, which exhibits a minimum molar heat capacity $c_p$ of 2.9 kJ/kmolK, and preferably of 2.5 kJ/kmolK. A typical range of $c_p$ is 1.9 to 2.7 kJ/kmolK.

In a further form of embodiment the polymer is chosen so that the softening occurs below a warming temperature of 250° C.

In a further form of embodiment the softening occurs below a softening temperature of 150° C., preferably under 100° C.

In another form of embodiment, apart from the implant itself, no other structural elements of the implant are provided for warming-up the implant.

In a further form of embodiment the medical implant comprises means for fastening a photoconductor with at least one light transmitting fiber.

In another form of embodiment the means consist of a recession or an elevation on the surface of the polymer.

In an additional form of embodiment, the coating capable of receiving appropriate colored substances upon contact with colored body fluids contains gypsum or calcium phosphate.

In one more form of embodiment the spectral absorption coefficient "a" of the color coating or of the reflecting coating is greater than 1,000 Mol$^{-1}$ cm$^{-1}$.

In another form of embodiment the spectral absorption coefficient "a" of the color coating or of the reflecting coating is greater than 1,000,000 Mol$^{-1}$ cm$^{-1}$.

In a further form of embodiment the absorption coefficient "a" of the color coating or of the reflecting coating is reduced by warming-up the polymer.

In another form of embodiment the absorption coefficient "a" is reduced by factor of at least 2, and preferably by a factor of 10.

In one more form of embodiment the absorption coefficient "a" of the color coating is reduced in a warmed-up condition of the polymer.

In another form of embodiment the absorption coefficient "a" of the color coating is reduced to at least one half in a warmed-up condition of the polymer.

In a further form of embodiment the absorption coefficient "a" of the color coating is reduced by a factor of at least 1.5, and preferably by a factor of 5.0 in a warmed-up condition of the polymer.

In one more form of embodiment the polymer to be warmed-up and softened is optically and/or mechanically isotropic.

In one more form of embodiment the polymer to be warmed-up and softened is optically and/or mechanically anisotropic.

In one more form of embodiment the polymer to be warmed-up and softened is a thermoplastic material.

In one more form of embodiment the thermoplastic material is chosen from the following groups: poly-alpha-hydroxyester, polyorthoester, polyanhydride, polyphosphazines, poly(propylenefumarate), polyesteramide, polyethylenefumarate, polyactide, polyglycolide, polycaprolacton, trimethylenecarbonate, polydioxanone, polyhydroxybutyrate, as well their copolymers and mixtures thereof.

Apart from the polymer containing a color material or being self-coloring, the medical implant or implant elements may also comprise additional materials, preferably chosen from the following groups: metals, carbon, ceramics, PEEK, non thermoplastic polymers that are preferably chosen from the group of polymethylmethacrylate and/or inorganic materials such as potassium phosphate, calcium sulphate or bone cement.

In another form of embodiment the polymer to be warmed-up and softened is a mat or an optically diffusing open-pore structure.

In a further form of embodiment the polymer to be warmed-up and softened has capillary channels.

In one more form of embodiment the polymer to be warmed-up and softened has hydrophilic characteristics.

In an additional form of embodiment the polymer to be warmed-up and softened is present in form of an implant layer.

In one more form of embodiment only a part of the surface of the implant is coated with the polymer to be warmed-up and softened.

In another form of embodiment the polymer to be warmed-up and softened comprises a zone with a variable absorption coefficient "a", in particular in the form of surface coatings.

In an additional form of embodiment the coating has a variable coating thickness.

In one more form of embodiment the spectral absorption coefficient "a" of the material has a low absorption coefficient "a" smaller than 1,000 mol$^{-1}$ cm$^{-1}$, and preferably smaller than 100 mol$^{-1}$ cm$^{-1}$.

In one more form of embodiment the polymer to be warmed-up and softened comprises a mixture of at least two thermoplastic materials compatible with the body.

In another form of embodiment the medical implant has a solid form.

In one more form of embodiment the polymer to be warmed-up and softened is present in a granulated form.

In a further form of embodiment the medical implant is produced of fibers, where the polymer to be warmed-up and softened preferably serves as a coating for the fibers.

In one more form of embodiment the medical implant is present in the form of an open-pore foam or sponge.

In a further form of embodiment the medical implant is conformed as a bone fixation element, preferably in the form of a bone screw, bone rod, bone dowel, pin, plate, dowel, hose (tube), thread, thread in a hose/tube or anchor (with a threading eyelet).

In one more form of embodiment the medical implant is conformed as a dental implant or dental root implant.

In one more form of embodiment the polymer to be warmed-up and softened is at least partially present in a softened condition.

In another form of embodiment the softened condition is generated by an electromagnetic radiation penetrating the polymer, preferably a light of a wavelength of 400-1,300 nm or a laser light.

In a further form of embodiment the polymer does not present a uniform photoconductivity, and on the surface of the implant the latter is preferably smaller than in the interior of the implant. This can achieve the advantage that thanks to the preferably internal radiation of the implant, the implant itself can be employed both as a mechanical support and stabilizer and as a photoconductor.

In various forms of embodiment of the process for the producing and/or the coating of a medical implant according to the invention, a color material or particle can be worked into a polymer by using one of the following variants:

1) An advantageous variant has turned out to be a compounding wherein the color material or particulate is worked into the fused mass and uniformly distributed into the polymer by shearing and mixing processes. The use of such compounds allows a direct production of implants or implant elements by an injection molding process.

If the application requires the availability of color-containing polymer layers or implant elements, these can be produced in a so-called two-component injection molding process. In this case, the uncolored part of the implant is injected in a first phase, and after modifying the cavity in the injection mold, the color containing part is injected in a second phase.

2) The layers of color-containing polymer are achieved by applying and drying the color and polymer containing solutions. It is in this case possible to achieve layers of color containing polymer by depositing and drying the color and polymer containing solutions, similar to a candle-drawing process (dip-coating process) or by spraying. The use of the first-mentioned depositing process allows achieving layers of a very thin (micrometer-thin) up to a very thick (sub- and millimeter range) size.

3) The at least one color layer is achieved by applying and drying a color-particles containing suspension or solution.

4) The coating occurs in the following steps:
a) Warming-up of color-containing particles;
b) Jetting the heated particles onto the surface of the uncolored part of the medical implant, so that the particles fuse the polymer of the uncolored part of the medical implant and are fixated on the surface.

Ceramic or other non-thermally sensitive particles can be applied to the surface by jetting them onto the polymer surface in a heated condition, where they can locally fuse the polymer and be fixated in the surface. An example for this is given by the plasma spraying process by which hip joint prostheses are for instance coated with calcium phosphate particles. The use of processes such as Chemical Vapor Deposition (CVD) or Physical Vapor Deposition (PVD) is also conceivable in the presence of suitable substrates.

The mentioned processes are also conceivable for an application of reflecting layers. The reflecting substances are in this case worked into the polymer by depositing a solution or suspension or by direct application or fusing onto the surface.

In another form of embodiment of the process for producing a medical implant according to the invention, the polymer is chosen so that the softening occurs above a warming-up temperature of 40° C.

In a preferred form of embodiment of the osteosynthesis process, the medical implant is, in an unsoftened condition, oversized with respect to the borehole in the bone.

In another form of embodiment of the osteosynthesis process, the medical implant in a non-softened condition is not oversized with respect to the borehole in the bone, and is in an internally pre-stressed condition.

In a further form of embodiment of the osteosynthesis process, the polymer to be warmed-up is introduced in the form of a rod through a hollow in the implant, or through a hollow instrument.

In one more form of embodiment of the osteosynthesis process, the polymer to be warmed-up and softened is introduced into an implant having a hollow space fitted with radially exiting holes.

The process steps used in applying a medical implant according to the invention are now described in closer detail, as follows:
a) Preparation of the bone, for instance by drilling out a borehole in the same;
b) Setting the fixation element, which is oversized with respect to the borehole, into the borehole;
c) Warming-up the (thermoplastic) implant polymer by irradiating it with light;
d) Inserting/pressing the partially liquefied implant/pin into the cavity, while filling out the various hollow spaces with their eventual ramifications; and
e) Allowing the implant to cool and solidify, which can be assisted for instance by active cooling.

EXAMPLE 1

Plate Osteosynthesis

An absorbable osteosynthesis plate of 1 mm thickness made of a poly-D,L-lactide was applied to the bone fragments to be fixated, and the necessary holes were drilled into the bone. In this example the plate was fitted with holes for 2 mm screws. Holes of 1.7 mm size were drilled into the bone. A partially light-conducting pin of 2.0 mm diameter was then passed through the screw hole in the plate, set up on the pre-drilled hole and impacted with light (at a power of 3 Watt and wavelength of 808 nm). The energy of the light flowed through the light conducting pin and warmed-up the same in the zone colored with carbon black. By applying a soft pressure on the pin, the pin could then be pushed into the pre-drilled hole in the bone, and the thermoplastic material could be made to flow into the accessible inter-trabecular interspaces in the cancellous bone. After turning off the light source, the polymer cooled off and solidified in less than one minute. The pin fitted with a somewhat oversized head (meaning a head larger than the borehole in the plate) was now locking the plate at the desired point.

EXAMPLE 2

Plate Osteosynthesis

In a variant of Example 1, a bone plate was used which had also been produced from the same polymer as the pin described above. The pin was inserted as in the above example. As soon as the head of the pin had come in contact with the plate, a fusion between the plate and the pin also occurred at this point, as in the region of the hole the plate was likewise light-absorbing and a fusion between the plate and the head could be achieved. After cooling, the pin and plate were firmly connected to each other, and the connection was locked at a stable angle.

EXAMPLE 3

Bone Anchor

The problem to be solved in this case was to fixate a thread in the bone, so as to lock up a tendon or other bone element with a thread. For this purpose a hole of a diameter of 3 mm and a depth up to 15 mm was drilled into the bone. A thread with a high fusing point was inserted into the hole in the bone. An anchor of a somewhat greater thickness than that of the hole itself was then set up on the hole.

in a manner similar to Example 1, the anchor was in this case also impacted with energy using a diode light, and after being softened up by the radiation energy, pressed into the bone. After turning off the light source, the solidified polymer and anchor were locked to the bone together with the thread.

EXAMPLE 4

Bone Anchor

In a modification of Example 3, the thread was passed through a transversally drilled hole in the anchor, the anchor was then inserted into the bone and fastened while using a glass fiber light source (fed by a lamp or laser source). The torn-off tendon was then fastened using the thread. The thread was in this case locked under a traction force. Thanks to the simultaneously switched-on light, the anchor partially fused and was glued to the thread under slight pressure, thus gaining a hold in the bone. After cooling within about 30 seconds, the traction force on the thread could be released. A knotting of the thread, which would otherwise have been necessary, could be omitted.

EXAMPLE 5

Implantation of a Prosthesis

In a dental implant made of titanium, the distal third was surrounded with a partially light-absorbing polymer. The implant itself was produced so as to be light-conductive (fitted with channels, from the side turned away from the tip of the root to the polymer). The light source was connected at this point. The implant was inserted into the hole that had been pre-drilled undersized, and the light was switched on. The polymer was warmed-up by the light and the implant could be pushed into the dental root channel. The solidification of the polymer after turning off the light in the bone led to a primary, load-resistant connection between the bone and the implant. The coating made of polylactide-co-glycolide degraded within a few days and allowed a growth of bone on the titanium implant thereafter.

EXAMPLE 6

Vascular Clip

The clip served to clamp-off blood vessels in order to prevent bleeding. It consisted essentially of two arms and a hinge. The arm was grasped with one clamp and the blood vessel was locked in the same. The arms were pressed together while admitting light. The implant was light-absorbing at the contact point between the arms and the hinge, but otherwise light-conductive. The light was conveyed to the contact point and the hinge through the clamp. The light thus softened the hinge and allowed bending the clip. Upon impacting the ends of the arms turned away from the hinge, a gluing together of the two arms occurred.

EXAMPLE 7

Reflection

A pin made of poly-D,L-lactide with a smooth surface of 7 mm length and 2.5 mm diameter was connected to a light source at its head, and inserted into a pre-drilled hole of 1.5 mm diameter. The light was introduced at the head of the pin and directed to the tip of the pin. In the region of the pin tip (turned away from the head of the pin) the implant was impacted and coated with gold vapor (the layer thickness was less than 0.1 mm in this application). The electromagnetic radiation was then reflected from the reflecting pin surface to the interior and bounced back. Although the pin material barely absorbed this radiation, the weak absorption of <30% sufficed to absorb the multiple reflected radiation and to locally warm-up the pin. The latter fused and could be pushed into the bone (meaning the borehole). The fused polymer penetrated into the inter-trabecular spaces and could, after turning off the light and cooling, gain a firm hold there.

It could be demonstrated in the laboratory that the light energy was generated by an intensified absorption in the polymer due to reflection, and not by the reflecting layer itself, because an irradiation of the implant from the outside could not achieve a softening of the polymer; only a radiation into the interior of the polymer across a non-reflecting zone could achieve the mentioned effect. However, certain forms of embodiment can be conceived of, wherein both a partial reflection and a partial absorption of the radiation can occur.

Moreover, a particular advantage of the reflection is the fact that as soon as the surface of the polymer fuses and deforms, the reflection abates and any further warming-up action is consequently slowed down. A local overheating can thus be prevented.

EXAMPLE 8

Plastic Vertebral Surgery

In an osteoporotic compression fracture of a lumbar vertebra, a hole of 4 mm diameter was drilled (under local anesthesia) from dorsal through the pedicles into the vertebral body (length ab. 4 cm). A partially colored pin made of poly-D,L-lactide (diameter 3.9 mm) was passed from dorsal and still without light effects through the hole, which had been filled with carbon black and thus achieved a resulting light absorption of 85% on its surface. The light source was then switched on and the pin was pushed into the vertebral body. An after-pushing of the pin could thus achieve a filling of the vertebral body with the poly-D,L-lactide. After a 2-minute cooling, the vertebral body was load-resistant.

EXAMPLE 9

Filling of Defects

The same pin as described in Example 8 was also employed for the filling of a bone defect, in this case of a tibia head defect. For this purpose, in the patient with the tibia head fracture a 4 mm diameter, 2 cm deep hole was drilled from ventral through the corticalis toward the defect. The pin was then pushed through this hole into the medullary and the cancellous space of the bone while applying light, thus creating a stable bone as in a composite osteosynthesis. The screws subsequently introduced in this area provided an excellent hold in the fused polymer. It has been proven that the subsequent fusing-in of polymer in recumbent osteosynthesis materials or recumbent prostheses leads to similarly stable conditions.

EXAMPLE 10

Composite Osteosynthesis

In the context of a collum femoris fracture in an osteoporosis condition, a dynamic hip screw was implanted through the collum femoris, which had been modified as follows: fitted internally with an additional longitudinal borehole of 3 mm diameter, and at the threaded tip with 10 radial holes of 1 mm diameter allowing a communication between the central borehole and the bone. A pin of 2.9 mm diameter, produced as in the example 9, was then inserted in this central borehole and impacted with light from the rear. Under the effect of the light, the pin could be fused inside the screw and the liquefied polymer penetrated through the holes outwardly into the bone, thus creating an augmentation of the bone wherein the implant locked up. After a 2-minute cooling of the polymer, the screw was load-resistant.

EXAMPLE 11

Memory Effect

A partially light-absorbing bone anchor was produced with an internal pre-stressing by injection molding (amorphous PLA). In the resulting cooled-down form, the anchor was straight (length 10 mm, diameter 3 mm). While using a thread passed through an eyelet in the upper third of the anchor, the anchor was pushed under soft pressure into a pre-drilled hole in the outer malleolus. Under the action of heat induced by the applied light, a relaxation of the anchor was started and the same bent over. This caused the anchor to jam in the hole and gain a hold in the same. The thread on the anchor could thus be loaded after 30 seconds and employed for reconstructing a bone.

EXAMPLE 12

Nail Locking

A medullary nail for a thigh bone was inserted into the thigh bone for an osteosynthesis. However, in this 86-year old female patient the bone was distally too soft for a locking operation, the operator thus drilled a 4 mm hole from lateral through the corticalis toward the nail. A 3.5 mm pin was pushed through the hole toward the nail. The pin was then impacted with light and pushed into the medullary, where it continuously fused onto the nail while filling up the medullary and embedding the nail. In order to properly distribute the implant material in the medullary hollow, a relatively high level of energy (70 Watt) and a polymer of high thermal capacity was chosen, so as to prevent an excessively rapid cooling and solidification. After turning off the light, the nail was securely fixated at the center of the thigh bone.

Figures 7A, 7B:
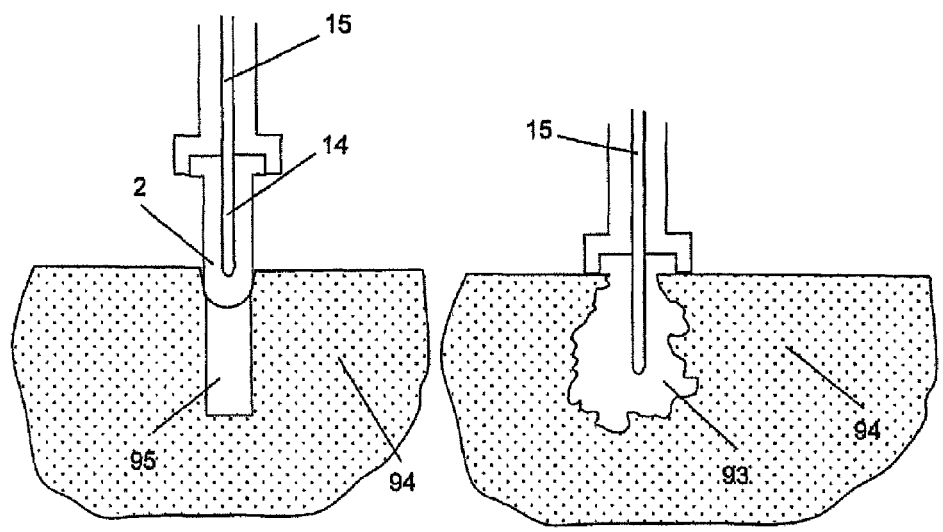
Figure 8:
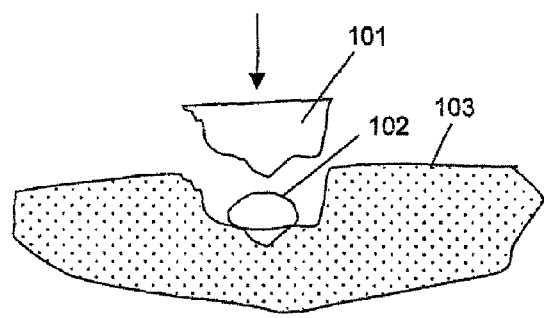
Figure 10:
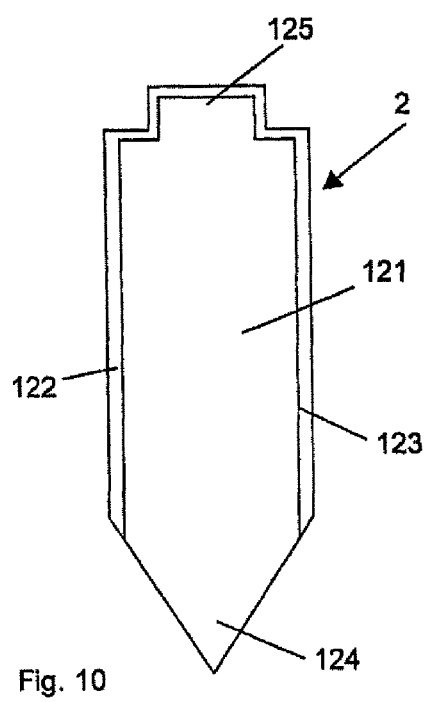
Figure 11:
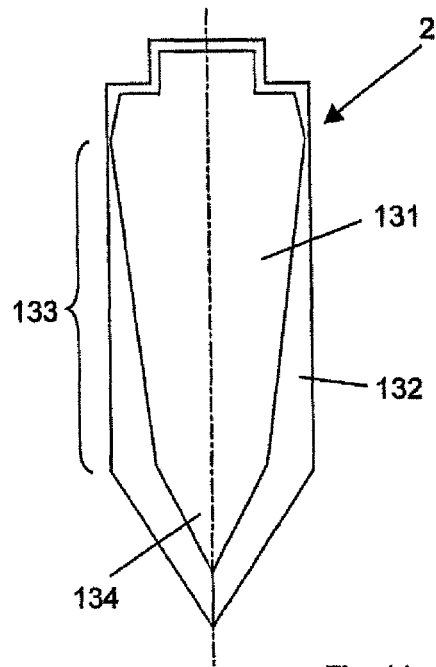
Figure 12:
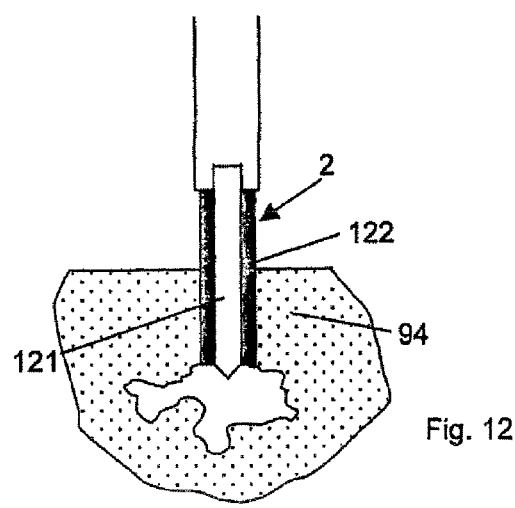
Figure 13A:
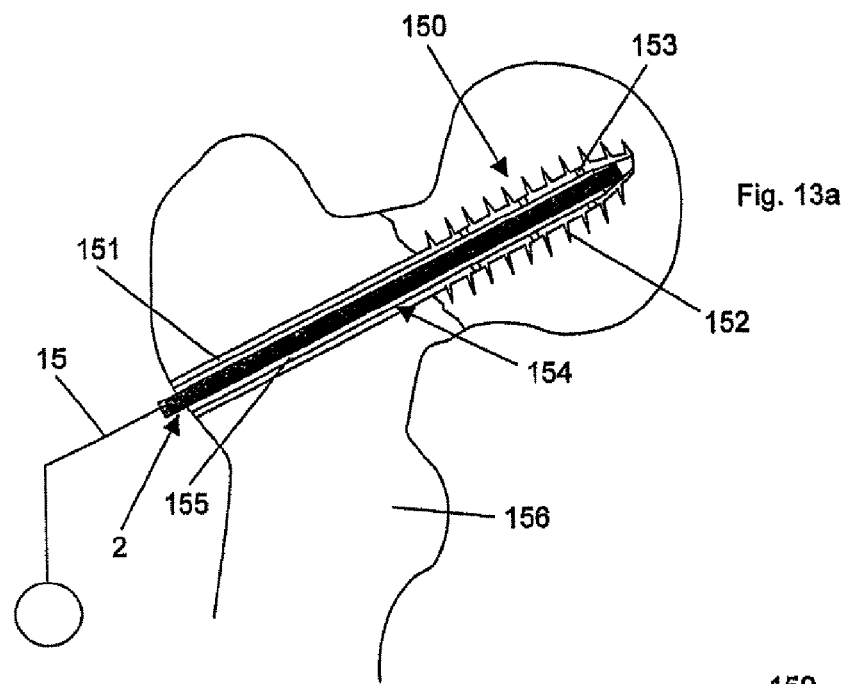

The invention and improvements of the invention will in the following, with the aid of partially simplified drawings of various examples of embodiments, be explained in greater detail. The drawings show:

FIG. 1: A longitudinal section through a form of embodiment of the medical implant according to the invention;

FIG. 2a: A cross section through another form of embodiment, conformed as a dental implant, of the medical implant according to the invention prior to the fusing process;

FIG. 2b: A cross section through a form of embodiment according to FIG. 3a, after a completed implantation;

FIG. 3a: A view of another form of embodiment of the medical implant according to the invention;

FIG. 3b: A view of the form of embodiment according to FIG. 3a, after a completed implantation;

FIG. 4a: A view of another form of embodiment of the medical implant according to the invention;

FIG. 4b: A view of the form of embodiment according to FIG. 4a, after a completed implantation;

FIG. 5a: A view of another form of embodiment of the medical implant according to the invention;

FIG. 5b: A view of the form of embodiment according to FIG. 5a, after a completed implantation;

FIG. 6a: A section through another form of embodiment of the medical implant according to the invention;

FIG. 6b: A section through the form of embodiment according to FIG. 6a, after a completed implantation;

FIG. 7a: A section through another form of embodiment of the medical implant according to the invention;

FIG. 7b: A section through the form of embodiment according to FIG. 7a, after a completed implantation;

FIG. 8: A section through another form of embodiment of the medical implant according to the invention;

FIG. 9a: A section through another form of embodiment of the medical implant according to the invention;

FIG. 9b: A section through the form of embodiment according to FIG. 9a, during the implantation;

FIG. 9c: A section through the form of embodiment according to FIGS. 9a and 9b, after a completed implantation;

FIG. 10: A section through another form of embodiment of the medical implant according to the invention;

FIG. 11: A section through another form of embodiment of the medical implant according to the invention;

FIG. 12: A section through another form of embodiment of the medical implant according to the invention;

FIG. 13a: A section through another form of embodiment of the medical implant according to the invention; and FIG. 13b: A section through the form of embodiment according to FIG. 13a, after a completed implantation.

In the form of embodiment shown in FIG. 1, the medical implant according to the invention comprises a pin 2 and is employed for an application in a vertebral implantation (Example 9). A pin 2 made of poly-L-co-D,L-lactide is inserted, from dorsal through a pre-drilled hole 10 and still without an admission of light, into a pedicle of a vertebral body 12 to be treated.

After introducing the pin 2, the light is switched on and the pin 2 is pushed, together with its connected light conductor, into the vertebral body 12. The after-pushing of pin 2 can thus achieve a filling 3 of the vertebral body 12 with poly-L-co-D,L-lactide. After 2 minutes cooling the vertebral body is load-resistant and pain-free.

The form of embodiment illustrated in FIGS. 2a and 2b comprises a dental implant 30 made of titanium and surrounded by a layer 34 of amorphous poly-D,L-lactide. The coated end 33 turned away from the distal end 32 is impacted with light 25. The dental implant 30 is inserted into the pre-drilled undersized hole 10 and the light is switched on (FIG. 2a). As soon as the absorption of light occurs in the layer 34, the layer 34 softens and the dental implant 30 can then be pushed deeply into the hole 10 by applying pressure. Upon pressing the dental implant 30 into the hole 10, the thermoplastic material forming the layer 34 is pushed into the interspaces of the bone 31, so as to create a mechanical connection between the dental implant 30 and the bone 31. The solidification of the polymer, meaning of the layer 34 in the bone 31 leads to a primary, load resistant connection between the bone 31 and the dental implant 30 (FIG. 2b).

The FIGS. 3a and 3b illustrate another form of embodiment, wherein the pin 2 is, through an appropriate production process, such as by injection molding, provided with an internal strain and has a length L and a diameter D (FIG. 3a) in a cooled off condition. Thanks to a warming of the entire pin 2 by admitting radiation to one of the ends A, B, the thermoplastic material relaxes and the pin 2 shortens and increases in diameter (FIG. 3b), thus leading to a fixation in or on the surrounding tissue.

In the form of embodiment illustrated in FIGS. 4a and 4b, the medical implant is conformed as a clip 60. The clip 60 is conformed to a U-shape and comprises two arms 61, 62, whose free ends 63 each comprise an element made of poly-L-co-D,L-lactide. These colored elements 64, which are thicker than the arms 61, 62, are impacted with radiation energy by using light conductors (FIG. 4a). After switching on the light the clip 60 is squeezed, meaning that the two elements 64 are pressed together. The two elements 64 are warmed-up by using light absorption, soften-up at their contact points leaning together, and can thus be joined by applying pressure and fusing them together (FIG. 4b).

The clip 50 shown in FIGS. 5a and 5b differs from the clip shown in FIGS. 4a and 4b only by the fact that the clip 70 is produced from a single piece of poly-L-co-D,L-lactide material. The arms 71, 72 are grasped with a clamp 74, impacted with light through a light conductor 15', 15" respectively, and pressed together. Thanks to the radiation energy, the hinge 73 connecting the arms 71, 72 softens and allows a bending of the clip 70. When the ends of the arms 71, 72 turned away from the hinge 73 are impinging on each other, the desired connecting action of the two arms 71, 72 at the thickened ends opposite the arms 71, 72 occurs by fusion.

In the form of embodiment illustrated in FIGS. 6a and 6b, the medical implant comprises a thread 80 consisting of a material with a high point of fusion and an anchor made of a polymer. The thread 80 is to be fixated to the bone 81 so that for instance the thread 80 locks-up a tendon or other bone element. For this purpose, a hole 82 having a diameter of 3 mm is drilled to a depth of 15 mm into the bone 81. The thread 80 is then inserted in this hole 82 in the bone 81. An anchor 83 having a slightly greater diameter than the hole 82 is then set up on the hole 82. As in the Example 1, the anchor 83 is also impacted with radiation energy from a light, and after being softened by the light, pressed into the bone 81. After turning off the light, the conductive polymer solidifies and the anchor, together with the thread 80, is fixated in the bone 81.

The form of embodiment shown in FIG. 7a, 7b is suitable for the filling of any defect in the bone 94. As in the form of embodiment according to FIG. 1, a pin 2 is used which has a central, enclosed hollow space 14 at the tip of pin 2 to receive a light conductor 15. The light conductor 15 can be removed again after the pin 2 has fused, or can also be produced from a reabsorbing material. In order to fill a tibia head defect in a patient affected by a tibia head fracture, for instance, a hole 46 with a diameter of 4 mm and a length of 2 cm is drilled from ventral, through the corticalis, up to the defect. The pin 2, together with the light conductor 15, is then pushed through this hole 95 into the medullary and into the cancellous space of the bone while applying light, thus creating, as in a composite osteosynthesis, a stable bone by fusing the pin 2 and filling 93. The screws (not shown here) subsequently inserted into this filling 93 provide, in their initially fused and then solidified polymer material, an excellent hold.

FIG. 8 illustrates a form of embodiment wherein the polymer of the medical implant is conformed as a pearl. This pearl 102 can be inserted into the hollow space that forms when a bone fragment 101 is broken out of a bone 103. The adapting of the bone fragment 101 into the hollow space and the connecting of the bone fragment 101 with the bone 103 by fusing the pearl 102 and pressing the polymer into the interspaces in the bone fragment 101 and the bone 103 occurs by irradiating the pearl 102 with light, so as to allow it to warm-up and deform.

Figure 9:
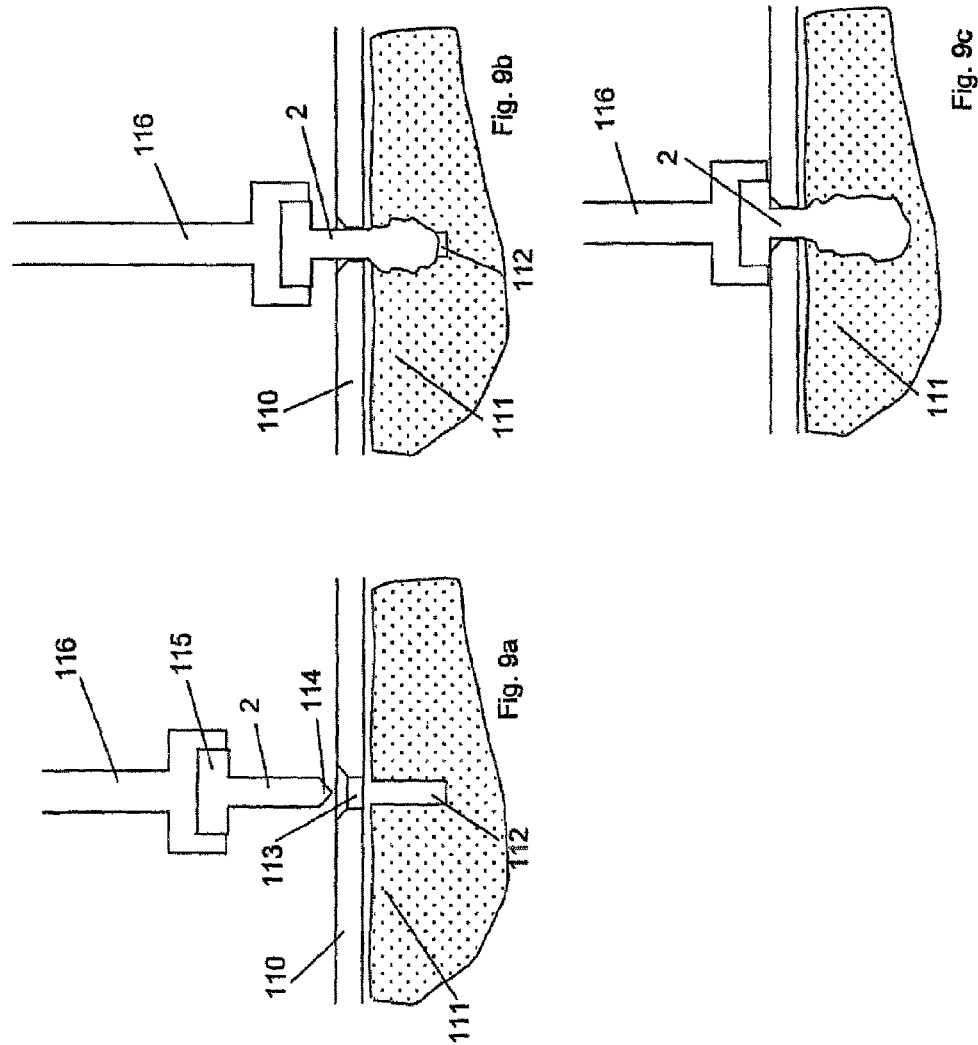

The form of embodiment shown in FIG. 9a-9c comprises a pin 2 made of poly-D,L-lactide, which is suitable for fixating a bone plate 110 on a bone 111. The bone plate 110 is a reabsorbing osteosynthesis plate with a thickness of 1 mm, made of the same material. In order to fixate a fracture, the bone plate 110 is applied to the bone fragments to be fixated, and the holes 112 needed for its fixating to the bone 111 are drilled into the bone 111. This example shows a bone plate 110 fitted with screw holes 113 for 2 mm screws. The holes 112 drilled into the bone 111 have a diameter of 1.5 mm. The pin 2 has a diameter of 2.0 mm and is applied with its enlarged-diameter rear head 115 to an instrument 116 (FIG. 9).

The light conductor can be passed coaxially through a central borehole (not shown) in the instrument 116.

The pin 2 with its tip 114 to be inserted into the bone 11 is passed though the screw hole 113 in the bone plate 110, set up on the hole 112 pre-drilled in the bone 111, and impacted with light. The supply of light energy through the pin 2 warms-up the same. The pin 2 is pushed into the hole 112 pre-drilled into the bone 111 by applying pressure to the instrument 15, and the thermoplastic material flows into the accessible intertrabecular interspaces in the cancellous bone (FIG. 9b). After turning off the light, the polymer cools off again and solidifies. The head 115 of the pin 2, which has a diameter larger than the screw hole 113 in the bone plate, now locks the bone plate 110 (FIG. 9c).

The FIGS. 10 and 11 each show a pin 2 which comprises a core 121, 131, made for instance of a metallic material, and a coating 122, 132 made of poly-D,L-lactide. The coating 122 in FIG. 10 is conformed like a bushing and extends over the cylindrical portion 123 and the rear end 125 of the pin 2. The tip 124 of the pin is formed without a coating. The coating 132 in FIG. 11 is only partially applied to a frontal section 133 of the pin 2, and encloses the tapering section 133 of the pin 2, including its tip 134 and rear end. A pin 2 conformed according to FIG. 10 or 11 allows a selective deformation of a thermoplastic material, so as to achieve its deformation.

FIG. 12 shows the application of a pin according to FIG. 10, for the filling of a defect in a bone 94 as shown in the FIGS. 7a and 7b.

Figure 13B:
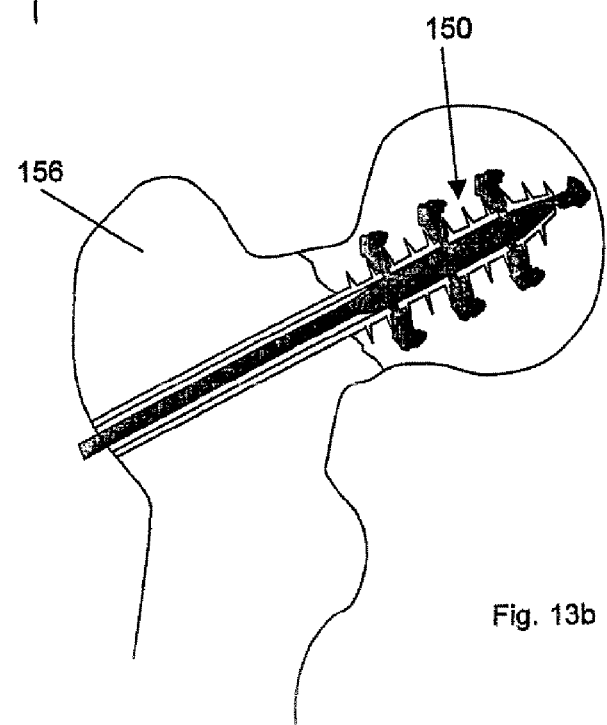

The FIGS. 13a and 13b illustrate a form of embodiment where the medical implant comprises a dynamic hip screw 150 and a pin 2 made of a polymer. The dynamic hip screw 150 has a hollow shaft 151 with a threaded borehole 152 on its frontal end extending up to the head of the hip point. The region of the threaded borehole 152 has radial perforations 153 that radially perforate the shaft 151 between its central hollow space 154 and its perimeter. Apart from the perforations 153, the hollow space 154 is fitted with an insulating coating 155. In the context of a collum femoris fracture, in case of an osteoporosis the dynamic hip screw 150 is implanted through the collum femoris. As described in Example 9, an isolated pin 2 of a diameter of 2.9 mm is then inserted into the central hollow space 154, and impacted with light, through a light conductor 15, at its rear end opposite the threaded borehole 152 of the dynamic hip screw 150. While absorbing light, the pin 2 thus fuses inside the hip screw 150, and the liquid polymer penetrates through the perforations 153 to the outside into the bone 156, thus creating an augmentation of the bone 156 in which the implant locks up. After the solidification of the polymer, the hip screw 150 is load-resistant (FIG. 13b).

The invention claimed is:

1. A medical implant for insertion into bone comprising:
   a zone sensitive to electromagnetic radiation from a radiation source, the zone comprising a polymer material configured to transition from a solid condition to a softened condition when the zone is exposed to the electromagnetic radiation and being flowable into interspaces of the bone in the softened condition; and
   a light-conducting portion configured to conduct the electromagnetic radiation from the radiation source to the zone when the medical implant is inserted into the bone, wherein the light-conducting portion comprises a transparent core and the zone is disposed around the light-conducting portion.

2. The medical implant of claim 1, wherein the zone comprises a colored layer or a reflecting layer.

3. The medical implant of claim 1, wherein the colored layer or the reflecting layer has a layer thickness of at least 0.01 μm.

4. The medical implant of claim 1, wherein a spectral absorption coefficient of the colored layer or the reflecting layer is greater than 1,000 Mol$^{-1}$ cm$^{-1}$.

5. The medical implant of claim 1, wherein an absorption coefficient of the colored layer is reducible by a factor of at least 1.5 when the polymer material transitions to the softened condition.

6. The medical implant of claim 1, wherein the polymer material has a minimum molar heat capacity $c_p$ of 1.6 kJ/kmolK.

7. The medical implant of claim 1, wherein the transition of the polymer material from the solid condition to the softened condition occurs below a temperature of 250° C.

8. The medical implant of claim 1, further comprising a depression or an elevation for fastening at least one light-conducting structure.

9. The medical implant of claim 1, wherein the polymer material is selected from the groups consisting of: poly-alpha-hydroxyester, polyorthoester, polyanhydride, polyphosphazenes, poly(propylenefumarate), polyesteramide, polyethylenefumarate, polylactide, polyglycolide, polycaprolacton, trimethylenecarbonate, polydioxanone, polyhydrobutyrate, as well as their copolymers and mixtures.

10. The medical implant according to claim 1, wherein the zone comprises regions with different absorption coefficients.

11. The medical implant of claim 1, further comprising fibers, wherein the zone coats the fibers.

12. The medical implant of claim 1, wherein the medical implant comprises an open-pore foam or sponge, a bone fixating element, or a dental implant or dental root implant.

13. An osteosynthesis process using the medical implant of claim 1 comprising:
   a) positioning of the medical implant outside an implanting point;
   b) exposing the zone to electromagnetic radiation until the polymer material transitions to the softened condition; and
   c) inserting the at least partially softened medical implant at the implanting point.

14. The medical implant of claim 1, further comprising a coating, the coating effective for receiving colored substances upon contact with body fluids containing the colored substances.

15. The medical implant of claim 1, wherein the medical implant comprises portions that do not soften when the polymer material transitions to the softened condition.

16. The medical implant of claim 1, wherein the zone comprises a colored component, a color-receiving component, and/or a reflective component.

17. A medical implant for insertion into bone comprising:
   a zone sensitive to electromagnetic radiation from a radiation source, the zone comprising a polymer material configured to transition from a solid condition to a softened condition when the zone is exposed to the electromagnetic radiation and being flowable into interspaces of the bone in the softened condition; and
   a light-conducting portion configured to conduct the electromagnetic radiation from the radiation source to the zone when the medical implant is inserted into the bone, wherein the light-conducting portion comprises a hollow space for receiving a light-conducting structure.

18. The medical implant of claim 17, wherein the zone comprises a colored layer or a reflecting layer.

19. The medical implant of claim 18, wherein the colored layer or the reflecting layer has a layer thickness of at least 0.01 μm.

20. The medical implant of claim 18, wherein a spectral absorption coefficient of the colored layer or the reflecting layer is greater than 1,000 Mol$^{-1}$ cm$^{-1}$.

21. The medical implant of claim 18, wherein an absorption coefficient of the colored layer is reducible by a factor of at least 1.5 when the polymer material transitions to the softened condition.

22. The medical implant of claim 17, wherein the polymer material has a minimum molar heat capacity $c_p$ of 1.6 kJ/kmolK.

23. The medical implant of claim 17, wherein the transition of the polymer material from the solid condition to the softened condition occurs below a temperature of 250° C.

24. The medical implant of claim 17, further comprising a depression or an elevation for fastening at least one light-conducting structure.

25. The medical implant of claim 17, wherein the polymer material is selected from the groups consisting of: poly-alpha-hydroxyester, polyorthoester, polyanhydride, polyphosphazenes, poly(propylenefumarate), polyesteramide, polyethylenefumarate, polylactide, polyglycolide, polycaprolacton, trimethylenecarbonate, polydioxanone, polyhydrobutyrate, as well as their copolymers and mixtures.

26. The medical implant according to claim 17, wherein the zone comprises regions with different absorption coefficients.

27. The medical implant of claim 17, further comprising fibers, wherein the zone coats the fibers.

28. The medical implant of claim 17, wherein the medical implant comprises an open-pore foam or sponge, a bone fixating element, or a dental implant or dental root implant.

29. An osteosynthesis process using the medical implant of claim 17 comprising:
   a) positioning of the medical implant outside an implanting point;
   b) exposing the zone to electromagnetic radiation until the polymer material transitions to the softened condition; and
   c) inserting the at least partially softened medical implant at the implanting point.

30. The medical implant of claim 17, further comprising a coating, the coating effective for receiving colored substances upon contact with body fluids containing the colored substances.

31. The medical implant of claim 17, wherein the medical implant comprises portions that do not soften when the polymer material transitions to the softened condition.

32. The medical implant of claim 17, wherein the zone comprises a colored component, a color-receiving component, and/or a reflective component.

* * * * *